United States Patent [19]

Devries et al.

[11] Patent Number: 4,473,579

[45] Date of Patent: Sep. 25, 1984

[54] ANTIATHEROSCLEROTIC TETRASUBSTITUTED UREAS AND THIOUREAS

[75] Inventors: Vern G. Devries, Ridgewood, N.J.; Ransom B. Conrow, Pearl River, N.Y.

[73] Assignee: American Cyanamid Company, Stamford, Conn.

[21] Appl. No.: 342,693

[22] Filed: Jan. 26, 1982

[51] Int. Cl.$^3$ ............... C07C 127/17; C07C 127/19; C07C 157/07; C07C 157/09; A61K 31/36; A61K 31/17

[52] U.S. Cl. ........................... 424/282; 424/304; 424/309; 424/317; 424/322; 260/465 D; 560/34; 562/439; 549/439; 564/48; 564/49; 564/50; 564/51; 564/52; 564/53; 564/54; 564/55; 564/26; 564/56

[58] Field of Search ............... 564/48, 49, 50, 52, 564/53, 54, 55, 56, 51; 424/322, 282, 304, 309, 317; 260/465 D; 562/439; 560/34; 549/439

[56] References Cited

U.S. PATENT DOCUMENTS

| | | | |
|---|---|---|---|
| 2,709,648 | 5/1955 | Ryker et al. | 564/53 X |
| 2,867,520 | 1/1959 | Beaver et al. | 564/53 X |
| 2,993,930 | 7/1961 | Chappelow et al. | 564/55 |
| 3,277,061 | 10/1966 | Fenton | 564/55 X |
| 3,326,663 | 6/1967 | Soloway et al. | 564/53 X |
| 3,483,296 | 12/1969 | Martin et al. | 564/53 X |
| 3,897,493 | 7/1975 | Teach | 564/48 |
| 4,010,281 | 3/1977 | Yamada et al. | 564/48 X |
| 4,127,673 | 11/1978 | Yamada et al. | 564/53 X |
| 4,349,526 | 9/1982 | Goor et al. | 564/48 X |

FOREIGN PATENT DOCUMENTS 6032447 4/1981 Japan .................. 564/53

OTHER PUBLICATIONS

Grammaticakis, CA 42:2515g (1948).
Chokki, CA 83:98851q (1975).
Mailhe, CA 13:2860$^7$ (1920).
Chappelow et al., J. Chem. Eng. Data 11 (3), p. 436–442 (1966).

*Primary Examiner*—Thomas A. Waltz
*Attorney, Agent, or Firm*—Jack W. Richards; Edward A. Conroy, Jr.

[57] ABSTRACT

Tetrasubstituted urea and thiourea compounds useful as antiatherosclerotic agents, compositions thereof and processes for their preparation.

20 Claims, No Drawings

ANTIATHEROSCLEROTIC TETRASUBSTITUTED UREAS AND THIOUREAS

BACKGROUND OF THE INVENTION

This invention relates to new tetrasubstituted urea and thiourea compounds useful as pharmaceutical agents. The novel compounds of the present invention are antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

A variety of urea and thiourea compounds can be found in the literature, for example, in *J. Med. Chem.* 18, 1024 (1975); *Chem. Absts.* 95: 6758m (1981) and 91: 74631 g (1979); U.S. Pat. Nos. 2,688,039; 3,335,142; 3,856,952; 3,903,130; and in West German Offenlegungsschrift No. 29 28 485. The compounds found in the literature are disclosed as being useful herbicides, plant growth regulators, bactericides, pesticides, fungicides, algacides, photographic sensitizers, antihelmintics, sympatholytics and antivirals. Those urea compounds found in Offenlegungsschrift No. 29 28 485 are disclosed as useful in inhibiting lipid absorption. There are, however, no literature references disclosing the tetrasubstituted urea and thiourea compounds of the present invention or their use in the treatment of atherosclerosis or hyperlipidemia.

Atherosclerosis is a form of arteriosclerosis characterized by lipid accumulation in and thickening of the arterial walls of both medium and large-sized arteries. Arterial walls are thereby weakened and the elasticity and effective internal size of the artery is decreased. Atherosclerosis is the most common cause of ischemic heart disease and is of great medical importance since the occlusion of medium and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plaques has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme Fatty acyl CoA:cholesterol acyl transferase or ACAT and the accumulation and storage of cholesteryl esters in the arterial wall is associated with increased activity of this enzyme [Hashimoto and Dayton, Atherosclerosis, 28, 447 (1977)]. In addition, cholesteryl esters are removed from cells at a slower rate than unesterified cholesterol [Bondjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesteryl esters in the arterial wall, and prevent or inhibit the formation and developoment of atheromatous lesions. The compounds of the present invention are very potent inhibitors of the ACAT enzyme. Thus, these compounds are useful for controlling and reducing the cholesteryl ester content of mammalian arterial walls, and decreasing the accumulation and storage of cholesterol in the arterial walls of mammals. Further, the compounds of this invention inhibit the formation or development of atherosclerotic lesions in mammals.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis, et al., 1974).

We have now found that certain members of this class of compounds can safely and effectively lower both serum lipids in warm-blooded animals. Such action on serum lipids is considered to be very useful in the treatment of atherosclerosis. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease and to stroke.

The compounds of this invention exhibit antiatherosclerotic activity and the invention should not be construed as limited to any particular mechanism of antiatherosclerotic action.

SUMMARY OF THE INVENTION

This invention relates to new tetrasubstituted urea and thiourea compounds, their preparation, pharmaceutical compositions containing them, and their use in the treatment of atherosclerosis. More particularly, it is concerned with ureas and thioureas which may be represented by formula I:

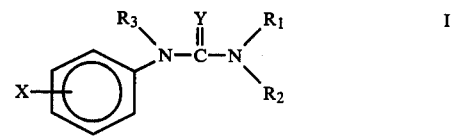

wherein X represents at least one substituent selected from the group consisting of hydrogen, $C_1$–$C_4$ alkyl, $C_1$–$C_4$ alkenyl, $C_1$–$C_4$ alkynyl, hydroxy, $C_1$–$C_4$ alkoxy, phenoxy, mercapto, $C_1$–$C_4$ alkylthio, amino, $C_1$–$C_4$ alkylamino, di-($C_1$–$C_4$ alkyl)amino, halo, trihalomethyl, $C_1$–$C_4$ alkanoyl, benzoyl, $C_1$–$C_4$ alkanamido, $C_1$–$C_4$ alkanesulfonyl, $C_1$–$C_4$ alkanesulfinyl, benzenesulfonyl, toluenesulfonyl, nitro, cyano, carboxy, $C_1$–$C_4$ carboalkoxy, carbamoyl, sulfamyl, methylenedioxy, phenyl, ortho-phenylene, tolyl, benzyl, halobenzyl, methylbenzyl and the group

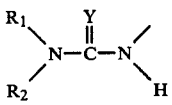

wherein Y is selected from the group consisting of oxygen and sulfur; $R_1$ and $R_2$ are the same or different and are independently selected from the group consisting of $C_4$–$C_{12}$ alkyl, $C_4$–$C_{12}$ alkenyl, $C_4$–$C_{12}$ alkynyl, $C_4$–$C_{12}$ cycloalkyl, $C_4$–$C_{12}$ cycloalkylalkyl, $C_7$–$C_{14}$ aralkyl, and $C_7$–$C_{14}$ aralkyl in which an aromatic ring bears at least one substituent selected from the group consisting of $C_1$–$C_{10}$ alkyl, $C_1$–$C_{10}$ alkoxy, phenoxy, benzyloxy, methylenedioxy, $C_1$–$C_{14}$ alkylthio, phenyl, halo, trihalomethyl, adamantyl, $C_1$–$C_4$ carboalkoxy, and nitro; $R_3$ is selected from the group consisting of $C_1$–$C_4$ alkyl, $C_1$–$C_4$ alkenyl, $C_1$–$C_4$ alkynyl, benzyl, benzyl bearing at least one substituent Z, naphthyl, phenyl and phenyl bearing at least one substituent Z, Z being selected independently of X from the group consisting of those from which X is selected.

Preferred embodiments of the invention are those in which Y is oxygen. More preferred are those in which X represents at least one $C_1$–$C_4$ alkyl or halo substituent and $R_1$ and $R_2$ are the same or different and are independently selected from the group consisting of $C_4$–$C_{12}$ alkyl, $C_7$–$C_{14}$ aralkyl and substituted $C_7$–$C_{14}$ aralkyl. The most preferred are those in which X represents at least one methyl or chloro substituent and Z is hydrogen, methyl or chloro.

Preferred specific embodiments involve:
1,1-dibenzyl-3-(2,4-dimethylphenyl)-3-phenylurea
1,1-dibenzyl-3-(3-chloro-4-methylphenyl)-3-phenylurea
1,1-di-(n-butyl)-3-(2,4-dimethylphenyl)-3-phenylurea
1,1-di-(n-butyl)-3-(3-chloro-4-methylphenyl)-3-phenylurea
1,1-dibenzyl-3,3-di-(2,4-dimethylphenyl)urea
1,1-dibenzyl-3,3-di-(3-chloro-4-methylphenyl)urea
1,1-di-(n-butyl)-3,3-di-(2,4-dimethylphenyl)urea
1,1-di-(n-butyl)-3,3-di-(3-chloro-4-methylphenyl)urea
1-benzyl-1-(n-butyl)-3-(2,4-dimethylphenyl)-3-phenylurea
1-benzyl-1-(n-butyl)-3-(3-chloro-4-methylphenyl)-3-phenylurea
1-benzyl-1-(n-butyl)-3,3-di-(2,4-dimethylphenyl)urea
1-benzyl-1-(n-butyl)-3,3-di-(3-chloro-methylphenyl)urea This invention also relates to a method of reducing the cholesterol content of the arterial walls of mammals which comprises administering to said mammal an effective amount of a compound as recited above.

This invention also relates to a method of treating hyperlipidemia in mammals which comprises administering to said mammal an effective amount of a compound as recited above.

This invention further relates to a method of inhibiting atherosclerotic lesion development in mammals which comprises administering to said mammal an effective amount of a compound as recited above.

This invention still further relates to a pharmaceutical composition which comprises and effective antiatherosclerotic amount of a compound as recited above in association with a pharmaceutically acceptable carrier.

Finally, this invention relates to processes for preparing compounds as recited above. One process useful for the preparation of the tetrasubstituted ureas and thioureas of this invention involves reacting a compound of formula II; wherein A and B are leaving groups, which may be the same or different, selected from the group consisting of halo, $C_1$–$C_4$ alkoxy, $C_1$–$C_4$ alkylthiophenoxy, 4-chlorophenoxy and 4-nitrophenoxy; with a secondary amine of formula III to yield an intermediate of formula IV and then reacting the intermediate with an arylamine of formula V, wherein X, Y, $R_1$, $R_2$ and $R_3$ are as defined above.

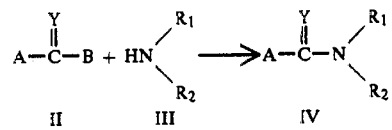

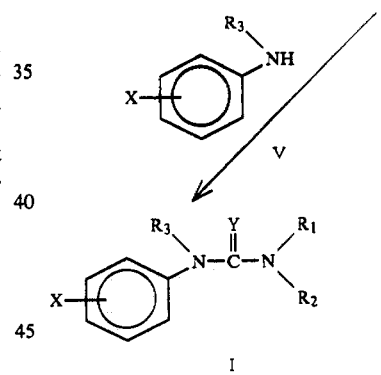

A second process for the preparation of tetrasubstituted ureas and thioureas involves reacting a compound of formula II with an arylamine of formula V to yield an intermediate of formula VI; wherein X, Y and $R_3$ are as defined above and then reacting the intermediate with a secondary amine of formula III; wherein $R_1$ and $R_2$ are as defined above.

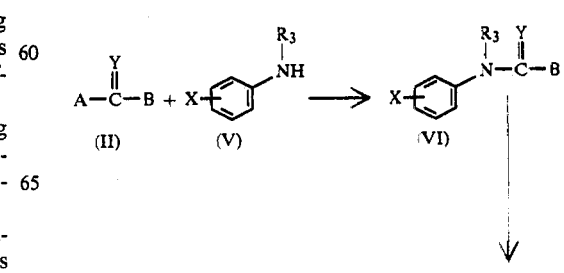

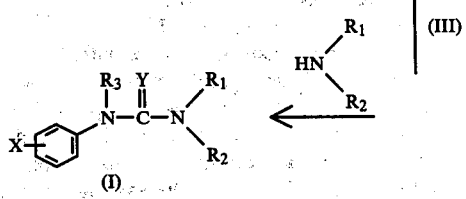

DETAILED DESCRIPTION OF THE INVENTION

Certain of the novel ureas and thioureas of this invention are prepared by reacting activated derivatives of carbonic acid such as phosgene, thiophosgene, or phenyl chloroformate with secondary amines to yield an intermediate, for instance, a disubstituted carbamyl chloride. This intermediate is in turn reacted with an arylamine to yield the urea or thiourea. The preparation of the intermediate is conducted in an aprotic solvent such as tetrahydrofuran, toluene, xylene, or the like at temperatures from about room temperature up to the boiling point of the solvent. The intermediate may be isolated by evaporation and purified by distillation if necessary. The intermediate is then reacted with an arylamine in an aprotic solvent such as dimethylacetamide in the presence of a base such as sodium hydride at temperatures from about room temperature up to the boiling point of the solvent used. An example of this process is the reaction of phosgene with N-benzyl-n-butylamine in toluene to yield the intermediate N-benzyl-N-(n-butyl)carbamyl chloride, which is then reacted with diphenylamine in N,N-dimethylacetamide in the presence of sodium hydride to yield 1-benzyl-1-(n-butyl)-3,3-diphenylurea.

Other of the novel ureas and thioureas of this invention are prepared by reacting arylamines with activated derivatives of carbonic acid such as phosgene or thiophosgene to yield an intermediate, for instance, an arylcarbamyl chloride. This intermediate is then reacted with a secondary amine to yield the urea or thiourea. The preparation of this intermediate is conducted in an aprotic solvent such as toluene or xylene at temperatures from about room temperature up to the boiling point of the solvent in the presence of a base, for example, N,N-dimethylaniline. The intermediate is then reacted with a secondary amine in an aprotic solvent such as toluene at temperatures from room temperature or below up to the boiling point of the solvent. An example of this process is the reaction of phosgene with N-phenyl-3-chloroaniline to yield the intermediate N-(3-chlorophenyl)-N-phenyl carbamyl chloride which is then reacted with N-benzyl-n-butylamine to yield 1-benzyl-1-(n-butyl)-3-(3-chlorophenyl)-3-phenylurea.

The ureas and thioureas of this invention which contain carboxy groups are prepared by alkaline hydrolysis of the corresponding carboalkoxy ureas and thioureas, prepared by the synthetic methods described above. Likewise, those which contain hydroxy, mercapto, or amino groups are prepared by alkaline hydrolysis of the corresponding O-acetyl, S-acetyl and N-acetyl ureas and thioureas, respectively, the latter also having been obtained by the urea and thiourea syntheses described above. Alternatively, ureas and thioureas containing hydroxy groups are prepared by cleavage of the corresponding methoxy compounds using Lewis acids such as boron tribromide.

Certain substituted N-benzylanilines which are intermediates required for the synthesis of some of the novel tetrasubstituted ureas and thioureas of this invention are not known in the art. The requisite N-benzylanilines are prepared by reactions of various benzaldehydes with anilines to yield anils. The anils are then reduced to yield the substituted N-benzylanilines. An example of such a synthesis involves the reaction of 2,4-dimethylbenzaldehyde with 2,4-dichloroaniline to yield N-(2,4-dimethylbenzylidene)-2,4-dichloroaniline followed by reduction with sodium borohydride to yield N-(2,4-dimethylbenzyl)-2,4-dichloroaniline.

The ureas and thioureas of the present invention are obtained as crystalline solids or distillable liquids. They are characterized by distinct melting or boiling points and unique spectra. They are appreciably soluble in organic solvents but generally less soluble in water. Those compounds which contain carboxylic acid groups may be converted to their alkali metal and alkaline earth salts by treatment with the appropriate metal hydroxides and those which contain amino groups may be converted to their ammonium salts by treatment with organic or mineral acids. Both of these types of salts exhibit increased water solubility.

The preparation and properties of the compounds of this invention will be described in greater detail in conjunction with the specific examples shown below.

The compounds of the present invention were assayed for two types of biological activity related to their potential use as antiatherosclerotic agents. Compounds were tested in vitro for their ability to inhibit the enzyme fatty acyl CoA:cholesterol acyl transferase (ACAT) and in vivo for serum hypolipidemic activity as measured by their ability to inhibit lipid absorption in rats. The compounds were tested for their ability to inhibit ACAT according to the following procedure:

Rat adrenals were homogenized in 0.2M monobasic potassium phosphate buffer, pH 7.4, and centrifuged at 1000 times gravity for 15 minutes at 5° C. The supernatant, containing the microsomal fraction, served as the source of the cholesterol-esterifying enzyme, fatty acyl CoA:cholesterol acyl transferase (ACAT). A mixture comprising 50 parts of adrenal supernatant, 10 parts of albumin (BSA) (50 mg./ml.), 3 parts of test compound (final concentration 5.2 g./ml.) and 500 parts of buffer was preincubated at 37° C. for 10 minutes. After treatment with 20 parts of oleoyl CoA($^{14}$C-0.4 Ci) the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesteryl ester fraction was counted in a scintillation counter. This procedure is a modification of that described by Hashimoto, et al., Life Scie., 12 (Part II), 1-12 (1973).

The results of this test on representative compounds of this invention appear in Table I.

TABLE I

| Compound | % Inhibition |
|---|---|
| 1-Benzyl-1-(n-butyl)-3,3-diphenylurea | 75.9 |
| 1-Benzyl-1-(n-butyl)-3-(3-chlorophenyl)-3-phenylurea | 72.3 |
| 1-Benzyl-1-(n-butyl)-3-(2-naphthyl)-3-phenylurea | 83.6 |

TABLE I-continued

| Compound | % Inhibition |
| --- | --- |
| 1-Benzyl-1-(n-butyl)-3-benzyl-3-phenylurea | 81.8 |
| 1-Benzyl-1-(n-butyl)-3-(3-methylphenyl)-3-phenylurea | 82.0 |
| 1-Benzyl-1-(n-butyl)-3-(3-methoxyphenyl)-3-phenylurea | 82.5 |
| 1-Benzyl-1-(n-butyl)-3-(4-isopropoxyphenyl)-3-phenylurea | 77.8 |
| 1-Benzyl-1-(n-butyl)-3-(1-naphthyl)-3-phenylurea | 76.3 |
| 1-Benzyl-1-(n-butyl)-3-(2-naphthyl)-3-(3-chlorophenyl)urea | 82.7 |
| 1-Benzyl-1-(n-butyl)-3,3-di-(2-naphthyl)urea | 93.2 |
| 1,3-Dibenzyl-1,3-di-(n-butyl)urea | 95.4 |

Inhibition of cholesterol absorption was determined by feeding male Sprague-Dawley rats, weighing 150-170 g., a 1% cholesterol: 0.5% cholic acid diet for 2 weeks. The diet was contained compounds being tested at a dose of 0.03% of the diet. Control rats were fed the same diet without any compound. At the end of the test, the rats were sacrificed by decapitation. Blood is collected, centrifuged at 1.5 kg times gravity for 10 minutes at 4° C., and the serum is then analyzed for cholesterol and triglycerides enzymatically by the method of Trinder, P., Analyst, 77, 321 (1952) on a Centrifichem 400 Analyzer. Livers are removed, a 0.4 g sample is taken from the center of the large lobe, and the sample is subjected to saponification using 25% saturated potassium hydroxide in ethanol. The resulting neutral sterols are extracted with petroleum ether and extract analyzed for cholesterol. The effectiveness of the compound in inhibiting cholesterol absorption is measured by the lowering of either serum cholesterol or liver cholesterol relative the values for control rats.

The results of this test on a typical compound of this invention appear in Table II.

TABLE II

| Compound | Result |
| --- | --- |
| 1-Benzyl-1-(n-butyl)-3-(3-methoxyphenyl)-3-phenylurea | Active |

The tests reported or shown in Tables I-II, inclusive, have been actually carried out and the results therein actually obtained or concluded therefrom.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5 and 60% by weight.

The antiatherosclerotic effective dosage of active ingredient employed may vary depending on the particular compound employed, the mode of administration and the severity of the condition being treated. However, in general, satisfactory results are obtained when the compounds of the invention are administered at a daily dosage of from about 2 mg. to about 500 mg./kg. of animal body weight, preferably given in divided doses two to four times a day, or in sustained release form. For most large mammals, the total daily dosage is from about 100 mg. to about 5,000 mg. preferably from about 100 mg. to 2,000 mg. Dosage forms suitable for internal use comprise from about 25 to 500 mg. of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be filled to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

EXAMPLE 1

1-Benzyl-1-(n-butyl)-3,3-diphenylurea

A solution of 20.0 g of phosgene in 100 ml. of toluene is stirred at 0° C. while a solution of 32.6 g. of N-benzyl-n-butylamine in 50 ml. of toluene is added during 15 minutes. The mixture is filtered and the filtrate is evaporated. The residue is evaporatively distilled at 105° C. under reduced pressure (250-350 microns) to yield N-benzyl-N-(n-butyl)carbamyl chloride as a colorless liquid.

A solution of 3.89 g. of diphenylamine in 25 ml. of dimethylacetamide is added during one hour to a stirred mixture of 5.19 g. of N-benzyl-N-(n-butyl)carbamyl chloride, 0.685 g. of sodium hydride, and 65 ml. of dimethylacetamide under a nitrogen atmosphere at 45°-50° C. The mixture is stirred for 2 hours at 50° C. and then poured into water. The mixture is extracted with methylene chloride and the extract is evaporated. The residue is purified by chromatography using silica gel as the adsorbant and acetone-hexane as the eluent. After evaporation of the eluent, the residue is evaporatively distilled at 165° C. under reduced pressure (150 microns) to yield 1-benzyl-1-(n-butyl)-3,3-diphenylurea as a viscous, clear, clorless liquid.

EXAMPLE 2

1-Benzyl-1-(n-butyl)-3-(3-chlorophenyl)-3-phenylurea

A solution of 5.09 g. of N-phenyl-3-chloraniline in 20 ml. of toluene is added to a solution of 4.70 g. of phosgene and 3.64 g. of N,N-dimethylaniline in 55 ml. of toluene and the mixture is warmed to 400° C. and then stirred while cooling to room temperature during 45 minutes. The mixture is extracted with water and the organic layer is separateld and evaporated to about one-half its volume. To this solution is added 100 ml. of toluene followed by 9.80 g. of N-benzyl-n-butylamine. The resulting mixture is sitrred under reflux for 30 minutes and then washed with water, 1N hydrochloric acid, and saturated sodium bicarbonate solution. The organic layer is separated, dried over sodium sulfate, decolorized using activated charcoal, and evaporated. The residue is evaporatively distilled at 185°-190° C. under reduced pressure (105 microns) to yield 1-benzyl-1-(n-butyl)-3-(3-chlorophenyl)-3-phenylurea as a viscous, pale-yellow liquid.

With reference to Examples 1 and 2 and Table III, only Examples 1-5; 9; 18; 40; 43; 99-100; 150-160; and 168 inclusive, have been actually carried out. Those compounds of the other actual Examples in Table III were prepared from the appropriate amines using phosgene or thiophosgene by the methods of Examples 1 and 2. All other Examples are simulated or predicted.

TABLE III

| Ex. | Compound | Melting Point |
|---|---|---|
| 3 | 1,3-Dibenzyl-1-(n-butyl)-3-phenylurea | yellow oil |
| 4 | 1-Benzyl-1-(n-butyl)-3-(2-naphthyl)-3-phenylurea | orange oil |
| 5 | 1-Benzyl-1-(n-butyl)-3-(3-methylphenyl)-3-phenylurea | oil |
| 6 | 1-Benzyl-1-(n-butyl)-3-(4-methylphenyl)-3-phenylurea | |
| 7 | 1-Benzyl-1-(n-butyl)-3-(3-ethylphenyl)-3-phenylurea | |
| 8 | 1-Benzyl-1-(n-butyl)-3-(4-ethylphenyl)-3-phenylurea | |
| 9 | 1-Benzyl-1-(n-butyl)-3-(4-isopropylphenyl)-3-phenylurea | amber oil |
| 10 | 1-Benzyl-1-(n-butyl)-3-(4-n-butylphenyl)-3-phenylurea | |
| 11 | 1-Benzyl-1-(n-butyl)-3-(2,3-dimethylphenyl)-3-phenylurea | |
| 12 | 1-Benzyl-1-(n-butyl)-3-(2,5-dimethylphenyl)-3-phenylurea | |
| 13 | 1-Benzyl-1-(n-butyl)-3-(2,6-dimethylphenyl)-3-phenylurea | |
| 14 | 1-Benzyl-1-(n-butyl)-3-(3,4-dimethylphenyl)-3-phenylurea | |
| 15 | 1-Benzyl-1-(n-butyl)-3-(3,5-dimethylphenyl)-3-phenylurea | |
| 16 | 1-Benzyl-1-(n-butyl)-3-(2,4,5-trimethylphenyl)-3-phenylurea | |
| 17 | 1-Benzyl-1-(n-butyl)-3-(2,4,6-trimethylphenyl)-3-phenylurea | |
| 18 | 1-Benzyl-1-(n-butyl)-3-(3-methoxyphenyl)-3-phenylurea | amber oil |
| 19 | 1-Benzyl-1-(n-butyl)-3-(4-n-butoxyphenyl)-3-phenylurea | |
| 20 | 1-Benzyl-1-(n-butyl)-3-(2,4-dimethoxyphenyl)-3-phenylurea | |
| 21 | 1-Benzyl-1-(n-butyl)-3-(4-methylthiophenyl)-3-phenylurea | |
| 22 | 1-Benzyl-1-(n-butyl)-3-(2-chlorophenyl)-3-phenylurea | |
| 23 | 1-Benzyl-1-(n-butyl)-3-(4-chlorophenyl)-3-phenylurea | |
| 24 | 1-Benzyl-1-(n-butyl)-3-(2-bromophenyl)-3-phenylurea | |
| 25 | 1-Benzyl-1-(n-butyl)-3-(4-bromophenyl)-3-phenylurea | |
| 26 | 1-Benzyl-1-(n-butyl)-3-(4-fluorophenyl)-3-phenylurea | |
| 27 | 1-Benzyl-1-(n-butyl)-3-(4-iodophenyl)-3-phenylurea | |
| 28 | 1-Benzyl-1-(n-butyl)-3-(2,3-dichlorophenyl)-3-phenylurea | |
| 29 | 1-Benzyl-1-(n-butyl)-3-(2,4-dichlorophenyl)-3-phenylurea | |
| 30 | 1-Benzyl-1-(n-butyl)-3-(2,5-dichlorophenyl)-3-phenylurea | |
| 31 | 1-Benzyl-1-(n-butyl)-3-(3,5-dichlorophenyl)-3-phenylurea | |
| 32 | 1-Benzyl-1-(n-butyl)-3-(2,4,6-trichlorophenyl)-3-phenylurea | |
| 33 | 1-Benzyl-1-(n-butyl)-3-(2,4-difluorophenyl)-3-phenylurea | |
| 34 | 1-Benzyl-1-(n-butyl)-3-(3-trifluoromethylphenyl)-3-phenylurea | |
| 35 | 1-Benzyl-1-(n-butyl)-3-(3-acetylphenyl)-3-phenylurea | |
| 36 | 1-Benzyl-1-(n-butyl)-3-(4-acetylphenyl)-3-phenylurea | |
| 37 | 1-Benzyl-1-(n-butyl)-3-(4-carboethoxyphenyl)-3-phenylurea | |
| 38 | 1-Benzyl-1-(n-butyl)-3-(4-phenoxyphenyl)-3-phenylurea | |
| 39 | 1-Benzyl-1-(n-butyl)-3-(2-cyanophenyl)-3-phenylurea | |
| 40 | 1-Benzyl-1-(n-butyl)-3-(3-chlorophenyl)-3-(2-naphthyl)urea | yellow oil |
| 41 | 1-Benzyl-1-(n-butyl)-3-(3-chloro-4-methylphenyl)-3-phenylurea | |
| 42 | 1-Benzyl-1-(n-butyl)-3-(2,6-dibromo-4-fluorophenyl)-3-phenylurea | |
| 43 | 1-Benzyl-1-(n-butyl)-3-(1-naphthyl)-3-phenylurea | amber oil |
| 44 | 1-Benzyl-1-(n-butyl)-3-(2-chloro-4-nitrophenyl)-3-phenylurea | |
| 45 | 1-Benzyl-1-(n-butyl)-3-(4-chloro-3-trifluoromethylphenyl)-3-phenylurea | |
| 46 | 1-Benzyl-1-(n-butyl)-3-(4-chloro-2-trifluoromethylphenyl)-3-phenylurea | |
| 47 | 1-Benzyl-1-(n-butyl)-3-(2-chloro-5-trifluoromethylphenyl)-3-phenylurea | |
| 48 | 1-Benzyl-1-(n-butyl)-3-(3,4-methylenedioxyphenyl)-3-phenylurea | |
| 49 | 1-Benzyl-1-(n-butyl)-3-(4-phenylphenyl)-3-phenylurea | |
| 50 | 1-Benzyl-1-(n-butyl)-3-(4-benzylphenyl)-3-phenylurea | |
| 51 | 1-Benzyl-1-(n-undecyl)-3-(2,4-dimethylphenyl)-3-phenylurea | |
| 52 | 1-Benzyl-1-(2-phenylethyl)-3-(2,4-dimethylphenyl)-3-phenylurea | |
| 53 | 1-Benzyl-1-(n-butyl)-3,3-di(2-methylphenyl)urea | |
| 54 | 1-Benzyl-1-(n-butyl)-3,3-di(3-methylphenyl)urea | |
| 55 | 1-Benzyl-1-(n-butyl)-3,3-di(4-methylphenyl)urea | |
| 56 | 1-Benzyl-1-(n-butyl)-3,3-di(3-ethylphenyl)urea | |

TABLE III-continued

| Ex. | Compound | Melting Point |
|---|---|---|
| 57 | 1-Benzyl-1-(n-butyl)-3,3-di(4-ethylphenyl)urea | |
| 58 | 1-Benzyl-1-(n-butyl)-3,3-di(4-isopropylphenyl)urea | |
| 59 | 1-Benzyl-1-(n-butyl)-3,3-di(4-n-butylphenyl)urea | |
| 60 | 1-Benzyl-1-(n-butyl)-3,3-di(2,3-dimethylphenyl)urea | |
| 61 | 1-Benzyl-1-(n-butyl)-3,3-di(2,5-dimethylphenyl)urea | |
| 62 | 1-Benzyl-1-(n-butyl)-3,3-di(2,6-dimethylphenyl)urea | |
| 63 | 1-Benzyl-1-(n-butyl)-3,3-di(3,4-dimethylphenyl)urea | |
| 64 | 1-Benzyl-1-(n-butyl)-3,3-di(3,5-dimethylphenyl)urea | |
| 65 | 1-Benzyl-1-(n-butyl)-3,3-di(2,4,5-trimethylphenyl)urea | |
| 66 | 1-Benzyl-1-(n-butyl)-3,3-di(2,4,6-trimethylphenyl)urea | |
| 67 | 1-Benzyl-1-(n-butyl)-3,3-di(4-methoxyphenyl)urea | |
| 68 | 1-Benzyl-1-(n-butyl)-3,3-di(4-n-butoxyphenyl)urea | |
| 69 | 1-Benzyl-1-(n-butyl)-3,3-di(2,4-dimethoxyphenyl)urea | |
| 70 | 1-Benzyl-1-(n-butyl)-3,3-di(4-methylthiophenyl)urea | |
| 71 | 1-Benzyl-1-(n-butyl)-3,3-di(2-chlorophenyl)urea | |
| 72 | 1-Benzyl-1-(n-butyl)-3,3-di(3-chlorophenyl)urea | |
| 73 | 1-Benzyl-1-(n-butyl)-3,3-di(4-chlorophenyl)urea | |
| 74 | 1-Benzyl-1-(n-butyl)-3,3-di(2-bromophenyl)urea | |
| 75 | 1-Benzyl-1-(n-butyl)-3,3-di(4-bromophenyl)urea | |
| 76 | 1-Benzyl-1-(n-butyl)-3,3-di(4-fluorophenyl)urea | |
| 77 | 1-Benzyl-1-(n-butyl)-3,3-di(4-iodophenyl)urea | |
| 78 | 1-Benzyl-1-(n-butyl)-3,3-di(2,3-dichlorophenyl)urea | |
| 79 | 1-Benzyl-1-(n-butyl)-3,3-di(2,4-dichlorophenyl)urea | |
| 80 | 1-Benzyl-1-(n-butyl)-3,3-di(2,5-dichlorophenyl)urea | |
| 81 | 1-Benzyl-1-(n-butyl)-3,3-di(3,5-dichlorophenyl)urea | |
| 82 | 1-Benzyl-1-(n-butyl)-3,3-di(2,4,6-trichlorophenyl)urea | |
| 83 | 1-Benzyl-1-(n-butyl)-3,3-di(2,4-difluorophenyl)urea | |
| 84 | 1-Benzyl-1-(n-butyl)-3,3-di(3-trifluoromethylphenyl)urea | |
| 85 | 1-Benzyl-1-(n-butyl)-3,3-di(3-acetylphenyl)urea | |
| 86 | 1-Benzyl-1-(n-butyl)-3,3-di(4-acetylphenyl)urea | |
| 87 | 1-Benzyl-1-(n-butyl)-3,3-di(4-carboethoxyphenyl)urea | |
| 88 | 1-Benzyl-1-(n-butyl)-3,3-di(4-phenoxyphenyl)urea | |
| 89 | 1-Benzyl-1-(n-butyl)-3,3-di(2-cyanophenyl)urea | |
| 90 | 1-Benzyl-1-(n-butyl)-3,3-di(3-chloro-2-methylphenyl)urea | |
| 91 | 1-Benzyl-1-(n-butyl)-3,3-di(3-chloro-4-methylphenyl)urea | |
| 92 | 1-Benzyl-1-(n-butyl)-3,3-di(2,6-dibromo-4-fluorophenyl)urea | |
| 93 | 1-Benzyl-1-(n-butyl)-3,3-di(2-nitro-4-methylphenyl)urea | |
| 94 | 1-Benzyl-1-(n-butyl)-3,3-di(2-chloro-4-nitrophenyl)urea | |
| 95 | 1-Benzyl-1-(n-butyl)-3,3-di(4-chloro-3-trifluoromethylphenyl)urea | |
| 96 | 1-Benzyl-1-(n-butyl)-3,3-di(4-chloro-2-trifluoromethylphenyl)urea | |
| 97 | 1-Benzyl-1-(n-butyl)-3,3-di(2-chloro-5-trifluoromethylphenyl)urea | |
| 98 | 1-Benzyl-1-(n-butyl)-3,3-di(3,4-methylenedioxyphenyl)urea | |
| 99 | 1-Benzyl-1-(n-butyl)-3,3-dibenzylurea | yellow oil |
| 100 | 1-Benzyl-1-(n-butyl)-3,3-di(2-naphthyl)urea | amber oil |
| 101 | 1-Benzyl-1-(n-butyl)-3,3-diphenylthiourea | |
| 102 | 1-Benzyl-1-(n-hexadecyl)-3,3-diphenylthiourea | |
| 103 | 1-Benzyl-1-(n-butyl)-3-(2-methylphenyl)-3-phenylthiourea | |
| 104 | 1-Benzyl-1-(n-butyl)-3-(3-methylphenyl)-3-phenylthiourea | |
| 105 | 1-Benzyl-1-(n-butyl)-3-(4-methylphenyl)-3-phenylthiourea | |
| 106 | 1-Benzyl-1-(n-butyl)-3-(3-ethylphenyl)-3-phenylthiourea | |
| 107 | 1-Benzyl-1-(n-butyl)-3-(4-ethylphenyl)-3-phenylthiourea | |
| 108 | 1-Benzyl-1-(n-butyl)-3-(4-isopropylphenyl)-3-phenylthiourea | |
| 109 | 1-Benzyl-1-(n-butyl)-3-(4-n-butylphenyl)-3-phenylthiourea | |
| 110 | 1-Benzyl-1-(n-butyl)-3-(2,3-dimethylphenyl)-3-phenylthiourea | |
| 111 | 1-Benzyl-1-(n-butyl)-3-(2,5-dimethylphenyl)-3-phenylthiourea | |
| 112 | 1-Benzyl-1-(n-butyl)-3-(2,6-dimethylphenyl)-3-phenylthiourea | |
| 113 | 1-Benzyl-1-(n-butyl)-3-(3,4-dimethylphenyl)-3-phenylthiourea | |
| 114 | 1-Benzyl-1-(n-butyl)-3-(3,5-dimethylphenyl)-3-phenylthiourea | |
| 115 | 1-Benzyl-1-(n-butyl)-3-(2,4,5-trimethylphenyl)-3-phenylthiourea | |
| 116 | 1-Benzyl-1-(n-butyl)-3-(2,4,6-trimethylphenyl)-3-phenylthiourea | |
| 117 | 1-Benzyl-1-(n-butyl)-3-(4-methoxyphenyl)-3-phenylthiourea | |
| 118 | 1-Benzyl-1-(n-butyl)-3-(4-n-butoxyphenyl)-3-phenylthiourea | |
| 119 | 1-Benzyl-1-(n-butyl)-3-(2,4-dimethoxyphenyl)-3-phenylthiourea | |
| 120 | 1-Benzyl-1-(n-butyl)-3-(4-methylthiophenyl)-3-phenylthiourea | |
| 121 | 1-Benzyl-1-(n-butyl)-3-(2-chlorophenyl)-3-phenylthiourea | |
| 122 | 1-Benzyl-1-(n-butyl)-3-(3-chlorophenyl)-3-phenylthiourea | |
| 123 | 1-Benzyl-1-(n-butyl)-3,3-di(2-methylphenyl)thiourea | |
| 124 | 1-Benzyl-1-(n-butyl)-3,3-di(3-methylphenyl)thiourea | |
| 125 | 1-Benzyl-1-(n-butyl)-3,3-di(4-methylphenyl)thiourea | |
| 126 | 1-Benzyl-1-(n-butyl)-3,3-di(3-ethylphenyl)thiourea | |
| 127 | 1 Benzyl-1-(n-butyl)-3,3-di(4-ethylphenyl)thiourea | |
| 128 | 1-Benzyl-1-(n-butyl)-3,3-di(4-isopropylphenyl)thiourea | |
| 129 | 1-Benzyl-1-(n-butyl)-1,1-di(4-n-butylphenyl)thiourea | |
| 130 | 1-Benzyl-1-(n-butyl)-1,1-di(1,2-dimethylphenyl)thiourea | |
| 131 | 1-Benzyl-1-(n-butyl)-1,1-di(2,5-dimethylphenyl)thiourea | |
| 132 | 1-Benzyl-1-(n-butyl)-1,1-di(2,6-dimethylphenyl)thiourea | |
| 133 | 1-Benzyl-1-(n-butyl)-1,1-di(1,4-dimethylphenyl)thiourea | |
| 134 | 1-Benzyl-1-(n-butyl)-1,1-di(1,5-dimethylphenyl)thiourea | |
| 135 | 1-Benzyl-1-(n-butyl)-1,1-di(2,4,5-trimethylphenyl)thiourea | |
| 136 | 1-Benzyl-1-(n-butyl)-1,1-di(2,4,6-trimethylphenyl)thiourea | |
| 137 | 1-Benzyl-1-(n-butyl)-1,1-di(4-methoxyphenyl)thiourea | |

TABLE III-continued

| Ex. | Compound | Melting Point |
|---|---|---|
| 138 | 1-Benzyl-1-(n-butyl)-1,1-di(4-n-butoxyphenyl)thiourea | |
| 139 | 1-Benzyl-1-(n-butyl)-1,1-di(2,4-dimethoxyphenyl)thiourea | |
| 140 | 1-Benzyl-1-(n-butyl)-1,1-di(4-methylthiophenyl)thiourea | |
| 141 | 1-Benzyl-1-(n-butyl)-1,1-di(chlorophenyl)thiourea | |
| 142 | 1,1-Dibenzyl-3-(2,4-dimethylphenyl)-3-phenylurea | |
| 143 | 1,1-Dibenzyl-3-(3-chloro-4-dimethylphenyl)-3-phenylurea | |
| 144 | 1,1-Di-(n-butyl)-3-(2,4-dimethylphenyl)-3-phenylurea | |
| 145 | 1,1-Di-(n-butyl)-3-(3-chloro-4-dimethylphenyl)-3-phenylurea | |
| 146 | 1,1-Dibenzyl-3,3-di(2,4-dimethylphenyl)urea | |
| 147 | 1,1-Dibenzyl-3,3-di(3-chloro-4-dimethylphenyl)urea | |
| 148 | 1,1-Di-(n-butyl)-3,3-di(2,4-dimethylphenyl)urea | |
| 149 | 1,1-Di-(n-butyl)-3,3-di(3-chloro-4-dimethylphenyl)urea | |
| 150 | 1-Benzyl-1-(n-butyl)-3-benzyl-3-(4-chlorophenyl)urea | oil |
| 151 | 1-Bnezyl-1-(n-butyl)-3-benzyl-3-(2,4-dimethylphenyl)urea | oil |
| 152 | 1-Benzyl-1-(n-butyl)-3-benzyl-3-(2,4-dichlorophenyl)urea | oil |
| 153 | 1-Benzyl-1-(n-butyl)-3-(3-nitrobenzyl)-3-(3,5-dimethoxyphenyl)urea | oil |
| 154 | 1-Benzyl-1-(n-butyl)-3-(2,4-dimethylbenzyl)-3-(2,4-dimethylphenyl)urea | oil |
| 155 | 1-Benzyl-1-(n-butyl)-3-(2,4-dichlorobenzyl)-3-(2,4-dichlorophenyl)urea | oil |
| 156 | 1-Benzyl-1-(n-butyl)-3-(2-chlorobenzyl)-3-(2-chlorophenyl)urea | oil |
| 157 | 1-Benzyl-1-(n-butyl)-3-(4-methylphenyl)-3-(4-methylbenzyl)urea | oil |
| 158 | 1-Benzyl-1-(n-butyl)-3-(2,4-dimethylbenzyl)-3-(2,4-dichlorophenyl)urea | oil |
| 159 | 1-Benzyl-1-(n-butyl)-3-(2,4-dichlorobenzyl)-3-(2,4-dimethylphenyl)urea | oil |
| 160 | 1-Benzyl-1-(n-butyl)-3-(3-chloro-4-methylbenzyl)-3-(4-methylphenyl)urea | oil |
| 161 | 1-Benzyl-1-(n-butyl)-3-(2,4-dimethylbenzyl)-3-phenyl urea | oil |
| 162 | 1-Benzyl-1-(n-butyl)-3-[3,5-di(trifluoromethyl)benzyl]-3-phenyl urea | oil |
| 163 | 1-Benzyl-1-(n-butyl)-3-(3-aminobenzyl)-3-)(3,5-dimethoxyphenyl) urea picrate | 156–158° |
| 164 | 1-Benzyl-1-(n-butyl)-3-benzyl-3-(3-aminophenyl)urea | 96–98° |
| 165 | 1-Benzyl-1-(n-butyl)-3-benzyl-3-(2,4,6-trimethylphenyl)urea | 63–69° |
| 166 | 1-Benzyl-1-(n-butyl)-3-benzyl-3-(3-nitrophenyl)urea | yellow oil |
| 167 | 1-Benzyl-1-(n-butyl)-3-(4-benzyloxybenzyl)-3-(4-carboethoxyphenyl)urea | |
| 168 | 1-Benzyl-1-(n-butyl)-3-benzyl-3-(3-acetamidophenyl)urea | oil |
| 169 | 1-Benzyl-1,3-di-(n-butyl)-3-phenylurea | |
| 170 | 1-Benzyl-1-(n-butyl)-3-(n-hexyl)-3-phenyl urea | |
| 171 | 1-Benzyl-1-(n-butyl)-3-(n-pentyl)-3-(2,4-dimethylphenyl)urea | |
| 172 | 1-Benzyl-1-(n-heptyl)-3-(n-octyl)-3-(2,4-dimethylphenyl)urea | |
| 173 | 1-Benzyl-1-(n-hexyl)-3-(n-butyl)-3-(3-chloro-4-methylphenyl) urea | |
| 174 | 1-(4-chlorobenzyl)-1-(4-methylbenzyl)-3-(n-hexyl)-3-(2,4-dimethylphenyl)urea | |

EXAMPLE 175

N-(2,4-Dimethylbenzylidene)-2,4-dichloroaniline

A mixture of 26.8 g. of 2,4-dimethylbenzaldehyde, 32.4 g. of 2,4-dichloroaniline, 0.20 g. of p-toluenesulfonic acid, and 150 ml of toluene is stirred under reflux using a Dean-Stark moisture trap. Evaporation of the mixture affords a solid which is recrystallized from ethanol to yield N-(2,4-dimethylbenzylidene)-2,4-dichloroaniline, mp 102°–106°.

Anilines prepared by the method of Example 175 are set forth in Table IV.

TABLE IV

| Ex. | Compound | Melting Point |
|---|---|---|
| 176 | N—benzylidene-2,4,6-trimethylaniline | yellow oil |
| 177 | N—benzylidene-2,4-dichloroaniline | 60–63° |
| 178 | N—(4-methylbenzylidene)-3-chloro-4-methylaniline | 86–89° |
| 179 | N—(2,4-dimethylbenzylidene)-2,4-dimethylaniline | 118–121° |
| 180 | N—(2,4-dichlorobenzylidene)-2,4-dimethylaniline | 105–107° |
| 181 | N—(3-nitrobenzylidene)-3,5-dimethoxyaniline | 113–116° |
| 182 | N—benzylidene-4-chloroaniline | 60–62° |
| 183 | N—benzylidene-2,4-dimethylaniline | oil |
| 184 | N—(2,4-dichlorobenzylidene)-2,4-dichloroaniline | 134–139° |
| 185 | N—(2-chlorobenzylidene)-2-chloroaniline | 111–117° |
| 186 | N—(4-methylbenzylidene)-4-methylaniline | 90–93° |
| 187 | N—benzylidene-3,5-di(trifluoromethyl)aniline | yellow oil |
| 188 | N—(4-benzyloxybenzylidene)-4-carboethoxyaniline | 140–142° |
| 189 | N—benzylidene-3-nitroaniline | 69–72° |

EXAMPLE 190

N-(2,4-Dimethylbenzyl)-2,4-dichloroaniline

A mixture of 13.9 g. of N-(2,4-dimethylbenzylidene)-2,4-dichloroaniline, 1.89 g. of sodium borohydride and 150 ml of ethanol is stirred under reflux for one hour, allowed to cool and poured into water. Recrystallization from ethanol yields N-(2,4-dimethylbenzyl)-2,4-dichloroaniline, m.p. 88°–90°.

Anilines prepared by the method of Example 190 are set forth in Table V.

TABLE V

| Ex. | Compound | Melting Point |
|-----|----------|---------------|
| 191 | N—benzyl-2,4,6-trimethylaniline | oil |
| 192 | N—benzyl-2,4-dichloroaniline | oil |
| 193 | N—(4-methylbenzyl)-3-chloro-4-methylaniline | oil |
| 194 | N—(2,4-dimethylbenzyl)-2,4-dimethylaniline | 72–7° |
| 195 | N—(2,4-dichlorobenzyl)-2,4-dimethylaniline | 70–72° |
| 196 | N—(3-nitrobenzyl)-3,5-dimethoxyaniline | amber oil |
| 197 | N—benzyl-4-chloroaniline | 48–49° |
| 198 | N—benzyl-2,4-dimethylaniline | 28–33° |
| 199 | N—(2,4-dichlorobenzyl)-2,4-dichloroaniline | 84–86° |
| 200 | N—(2-chlorobenzyl)-2-chloroaniline | 41–44° |
| 201 | N—(4-methylbenzyl)-4-methylaniline | 50–54° |
| 202 | N—benzyl-3,5-di(trifluoromethyl)aniline | oil |
| 203 | N—(4-benzyloxybenzyl)-4-carboethoxyaniline | 147–150° |
| 204 | N—benzyl-3-nitroaniline | 106–108° |

Example 175 and Examples 176–202, inclusive, in Tables IV and V have been actually carried out.

We claim:
1. A compound of the formula:

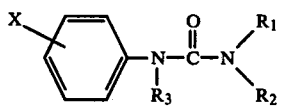

wherein X represents at least one substituent selected from the group consisting of ($C_1$–$C_4$)alkyl, ($C_1$–$C_4$)alkenyl, ($C_1$–$C_4$)alkynyl, phenoxy, mercapto, amino, ($C_1$–$C_4$)alkylamino, di($C_1$–$C_4$)alkylamino, halo, trihalomethyl, ($C_1$–$C_4$)alkanoyl, benzoyl, ($C_1$–$C_4$)alkanamido, nitro, cyano, carboxy, ($C_1$–$C_4$)-carboalkoxy, carbamoyl, sulfamyl, methylenedioxy, phenyl, ortho-phenylene, tolyl, benzyl, halobenzyl and the group

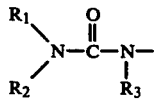

$R_1$ and $R_2$ are the same or different and are independently selected from the group consisting of ($C_4$–$C_{12}$)alkyl, ($C_4$–$C_{12}$)alkenyl, ($C_4$–$C_{12}$)alkynyl, ($C_4$–$C_{12}$)cycloalkylalkyl, ($C_7$–$C_{14}$)aralkyl, and ($C_7$–$C_{14}$)aralkyl in which an aromatic ring bears at least one substituent selected from the group consisting of ($C_1$–$C_{10}$)alkyl, ($C_1$–$C_{10}$)alkoxy, phenoxy, benzyloxy, methylenedioxy, ($C_1$–$C_4$)alklthio, phenyl, halo, trihalomethyl, adamantyl, ($C_1$–$C_4$)carboalkoxy and nitro; $R_3$ is selected from the group consisting of ($C_1$–$C_4$)alkenyl, ($C_1C_4$)alkynyl, benzyl, benzyl bearing at least one substituent Z, naphthyl, phenyl and phenyl bearing at least one substituent Z, Z being selected independently of X from the group consisting of those from which X is selected with the proviso that X may not be alkyl only.

2. A compound as recited in claim 1 wherein X represents at least one substituent selected from the group consisting of ($C_1$–$C_4$)alkyl, halo, carboxy, ($C_1$–$C_4$)carboalkoxy and benzyl.

3. A compound as recited in claim 2 wherein $R_1$ is ($C_7$–$C_{14}$)aralkyl and $R_2$ is ($C_4$–$C_{12}$)alkyl.

4. A compound as recited in claim 3 wherein $R_1$ is benzyl and $R_2$ is n-butyl.

5. The compound as recited in claim 1; 1,1-di-benzyl-3-(3-chloro-4-methylphenyl)-3-phenylurea.

6. The compound as recited in claim 1; 1,1-di-(n-butyl)-3-(3-chloro-4-methylphenyl)-3-phenylurea.

7. The compound as recited in claim 1; 1,1-di-benzyl-3,3-di-(3-chloro-4-methylphenyl(urea.

8. The compound as recited in claim 1; 1,1-di-(n-butyl)-3,3-di-(3-chloro-4-methylphenyl)urea.

9. The compound as recited in claim 1; 1-benzyl-1-(n-butyl)-3-(3-chloro-4-methylphenyl)-3-phenylurea.

10. The compound as recited in claim 1; 1-benzyl-1-(n-butyl)-3,3-di-(3-chloro-4-methylphenyl)urea.

11. The compound as recited in claim 1; 1-benzyl-1-(n-butyl)-3-(4-chlorophenyl)-3-phenylurea.

12. The compound as recited in claim 1; 1-benzyl-1-(n-butyl)-3-(3-chlorophenyl)-3-phenylurea.

13. A method of reducing the cholesterol ester content of an arterial wall, inhibiting atherosclerotic lesion development and treating hyperlipidemia in a mammal in need of such treatment which comprises administering to said mammal an effective amount of a compound as recited in claim 1.

14. A method of reducing the cholesterol ester content of an arterial wall in a mammal in need of such treatment which comprises administering to said mammal a cholesterol ester-reducing amount of a compound as recited in claim 1.

15. A method of inhibiting atherosclerotic lesion development in a mammal in need of such treatment which comprises administering to said mammal an atherosclerotic lesion development-inhibiting amount of a compound as recited in claim 1.

16. A method of treating hyperlipidemia in a mammal in need of such treatment which comprises administering to said mammal an effective lipid-altering amount of a compound as recited in claim 1.

17. A pharmaceutical composition suitable for reducing the cholesterol ester content of an arterial wall, inhibiting atherosclerotic lesion development and treating hyperlipidemia in a mammal which comprises an effective amount of a compound as recited in claim 1 and a non-toxic, pharmaceutically acceptable carrier.

18. A pharmaceutical composition suitable for reducing the cholesterol ester content of an arterial wall in a mammal which comprises a cholesterol ester-reducing amount of a compound as recited in claim 1 and a non-toxic pharmaceutically acceptable carrier.

19. A pharmaceutical composition suitable for inhibiting atherosclerotic lesion development in a mammal which comprises an atherosclerotic lesion development-inhibiting amount of a compound as recited in claim 1 and a non-toxic, pharmaceutically acceptable carrier.

20. A pharmaceutically composition suitable for treating hyperlipidemia in a mammal which comprises an effective lipid-lowering amount of a compound as recited in claim 1 and a non-toxic, pharmaceutically acceptable carrier.

* * * * *